(12) United States Patent
Halvorsen et al.

(10) Patent No.: US 7,033,587 B2
(45) Date of Patent: *Apr. 25, 2006

(54) USE OF ADIPOSE TISSUE-DERIVED STROMAL CELLS FOR CHONDROCYTE DIFFERENTIATION AND CARTILAGE REPAIR

(75) Inventors: Yuan-Di C. Halvorsen, Holly Springs, NC (US); William O. Wilkison, Bahama, NC (US); Jeffrey Martin Gimble, Chapel Hill, NC (US)

(73) Assignee: Artecel Sciences, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/980,137

(22) Filed: Nov. 1, 2004

(65) Prior Publication Data

US 2005/0112761 A1    May 26, 2005

Related U.S. Application Data

(60) Division of application No. 10/125,106, filed on Apr. 18, 2002, now Pat. No. 6,841,150, which is a continuation of application No. 09/573,989, filed on May 17, 2000, now Pat. No. 6,429,013.

(60) Provisional application No. 60/149,850, filed on Aug. 19, 1999.

(51) Int. Cl.
*C12N 5/00* (2006.01)

(52) U.S. Cl. .............. 424/93.7; 424/93.4; 435/325; 435/366; 435/377; 435/395; 435/455

(58) Field of Classification Search .......... 424/93.7, 424/93.4; 435/377, 325, 366, 395, 455
See application file for complete search history.

(56) References Cited

U.S. PATENT DOCUMENTS

| | | | |
|---|---|---|---|
| 4,362,567 A | 12/1982 | Schwarz et al. |
| 4,377,572 A | 3/1983 | Schwarz et al. |
| 5,160,490 A | 11/1992 | Naughton et al. |
| 5,197,973 A | 3/1993 | Pang et al. |
| 5,486,359 A | 1/1996 | Caplan et al. |
| 5,723,331 A | 3/1998 | Tubo et al. |
| 5,786,207 A | 7/1998 | Katz et al. |
| 5,863,531 A | 1/1999 | Naughton et al. |
| 5,902,741 A | 5/1999 | Purchio et al. |
| 5,908,784 A | 6/1999 | Johnstone et al. |
| 6,153,432 A | 11/2000 | Halvorsen et al. |
| 6,194,203 B1 | 2/2001 | Blum et al. |
| 6,200,606 B1 | 3/2001 | Peterson et al. |

FOREIGN PATENT DOCUMENTS

| | | |
|---|---|---|
| FR | 2 448 900 | 9/1980 |
| FR | 2 448 901 | 9/1980 |
| WO | WO 95/33821 A1 | 12/1995 |
| WO | WO 99/28444 A1 | 6/1999 |
| WO | WO 00/53795 A1 | 9/2000 |

OTHER PUBLICATIONS

U.S. Appl. No. 60/123,711, filed Mar. 10, 1999, Peterson et al.

U.S. Appl. No. 60/162,462, filed Oct. 29, 1999, Peterson et al.

Ashton et al., "Formation of Bone and Cartilage by Marrow Stromal Cells in Diffusion Chambers in Vivo," Clin. Orthop. Rel. Res., (1980), vol. 151, pp. 294-307.

Ballock & Reddi, "Thyroxine is the Serum Factor That Regulates Morphogenesis of Columar Cartilage from Isolated Chondrocytes in Chemically Defined Medium," J. Cell Biol., (1994), vol. 126:5, pp. 1311-1318.

Benya, P., et al., Dedifferentiated Chondrocytes Reexpress the Differentiated Collagen Phenotype When Cultured in Agarose Gels, Cell, 30 (1982), 215-224.

Bonadio et al., "Localized, Direct Plasmid Gene Delivery in Vivo: Prolonged Therapy Results In Reproducible Tissue Regeneration," Nat. Med., (1999), vol. 5, pp. 753-759.

Bruder et al., "Osteochondral Differentiation and the Emergence of State-Specific Osteogenic Cell-Surface Molecules by Bone Marrow Cells in Diffusion Chambers," Bone Mineral, (1990), vol. 11, pp. 141-151.

Burris et al., "A Novel Method for Analysis of Nuclear Receptor Function at Natural Promoters: Peroxisome Proliferator-Activated Receptor y Agonist Actions on a P2 Gene Expression Detected Using Branched DNA Messenger RNA Quantitation," Molecular Endocrinology, (1999), 13, 3, 410.

Byk T. et al., "Lipofectamine and Related Cationic Lipids Strongly Improve Adenoviral Infection Efficiency of Primitive Human Hematopoietic Cells," Human Gene Therapy, (1998), vol. 9, pp. 2493-2502.

(Continued)

*Primary Examiner*—Leon B. Lankford, Jr.
(74) *Attorney, Agent, or Firm*—Drinker Biddle & Reath LLP

(57) ABSTRACT

Methods and compositions for directing adipose-derived stromal cells cultivated in vitro to differentiate into cells of the chondrocyte lineage are disclosed. The invention further provides a variety of chondroinductive agents which can be used singly or in combination with other nutrient components to induce chondrogenesis in adipose-derived stromal cells either in cultivating monolayers or in a biocompatible lattice or matrix in a three-dimensional configuration. Use of the differentiated chondrocytes for the therapeutic treatment of a number of human conditions and diseases including repair of cartilage in vivo is disclosed.

19 Claims, 5 Drawing Sheets

OTHER PUBLICATIONS

Chu CR et al., "Articular Cartilage Repair Using Allogeneic Perichondrocyteseeded Biodegradable Porous Polyactic Acid (PLA): A Tissue-Engineering Study," J. Biomed. Mater. Res., (1995), vol. 29, pp. 1147-1154.

Dennis et al., "Osteogenesis in Marrow Derived Mesenchymal Cell Porous Ceramic Composites Transplanted Subcutaneously: Effect of Fibronectin and Laminin on Cell Retention and Rate of Osteogenic Expression," Cell Transpl. (1991), vol. 1, pp. 23-32.

Dorheim et al., "Osteoblastic Gene Expression During Adipogenesis in Hematopoietic Supporting Murine Bone Marrow Stromal Cells," J. Cell Physiol., (1993), vol. 154, pp. 317-328.

Elmer et al., "Immunohistochemical Localization of Cyclic AMP During Normal and Abnormal Chick and Mouse Limb Development," Teratology, (1981), vol. 24, pp. 215-223.

Gimble, Jeffrey Martin, "The Function of Adipocytes in the Bone Marrow Stroma," The New Biologist, (1990), 2, 4, 304.

Gimble et al., "Adipogenesis in a Myeloid Supporting Bone Marrow Stromal Cell Line," J. Cell Biochem., (1992), vol. 50, pp. 73-82.

Gimble et al., "The Function of Adipocytes in the Bone Marrow Stroma: An Update," Bone, (Nov. 1996), vol. 19:5, pp. 421-428.

Gimble et al., "Nuclear Hormone Receptors and Adipogenesis," Critical Reviews in Eukaryotic Gene Expression, (1998), 8(2), 141.

Gimble et al., "Adipocyte Biology of the Bone," Adipocyte Biology and Hormone Signaling, IOS Press, The Netherlands, (2000), 231.

Goshima et al., "The Origin of Bone Formed in Composite Grafts of Porous Calcium Phosphate Ceramic Loaded with Marrow Cells," Clin. Orthop. Rel. Res., (1991), vol. 269, pp. 274-283.

Gronthos et al., "Surface Protein Characterization of Human Adipose Tissue-Derived Stromal Cells," Journal of Cellular Physiology, (2001), 9999,1.

Hauschka, S. D., "Clonal Analysis of Vertebrate Myogenesis III. Developmental Changes in the Muscle-Colony-Forming Cells of the Human Fetal Limb," Development Biology, (1974), vol. 37, pp. 345-368.

Hendrickson DA et al., "Chondrocyte-Fibrin Matrix Transplants for Resurfacing Extensive Articular Cartilage Defects," Orthop. Res., (1994), vol. 12, pp. 485-497.

Ichinose et al., "Structure of Transglutaminases," J. Biol. Chem., (1990), vol. 265:3, pp. 13411-13414.

Kato et al., "Terminal Differentiation and Calcification in Rabbit Chondrocyte Cultures Grown in Centrifuge Tubes: Regulation by Transforming Growth Factor β and Serum Factors," PNAS, (1988), vol. 85, pp. 9552-9556.

Mackay et al., (1998), Tissue Engineering 4:415-428.

Mayne et al., "Changes in Type of Collagen Synthesized as Clones of Chick Chondrocytes Grown and Eventually Lose Division Capacity," PNAS, (1976), vol., 73:5, pp. 1674-1678.

Mayne et al., "Changes in the Synthesis of Minor Cartilage Collagens after Growth of Chick Chonrocytes in 5-Bromo-2'-Deoxyuridine or to Senscence," Exp. Cell. Res., (1984), vol. 151:1, pp. 171-182.

Mizudo, M.D., Hiroshi, "The Myogenic Potential of Human Processed Lipoaspirates—Part I: Morphological, Immunohistochemical Analysis and Gene Expression," J. Jpn. P.R.S., (2001), 21 427.

Mizuno et al., "Myogenic Differentiation by Human Processed Lipoaspirate Cells," Plastic and Reconstructive Surgery, (2002), 109, 1, 199.

Nakahara et al., "In Vitro Differentiation of Bone and Hypertrophic Cartilage from Periosteal-Derived Cells," Exp. Cell Res., (1981), vol. 195, pp. 492-503.

Oegama et al., "Characterization of a Hyaluronic Acid-Dermatan Sulfate Proteoglycan Complex from Dedifferentiated Human Chondrocyte Cultures," J. Biol. Chem., (1981) vol. 256:2, pp. 1015-1022.

Okayama et al., "Differences Among Sulfated Proteoglycans Synthesized in Nonchondrogenic Cells, Presumptive Chondroblasts, and Chondroblasts," PNAS, (1976), vol. 73:9, pp. 3224-3228.

Pacifici et al., "Transformation of Chondroblasts by Rous Sarcoma Virus and Synthesis of the Sulfated Proteoglycan Matrix," Cell, (1977), vol. 4, pp. 891-899.

Pacifici et al., "12-OTetradecanoylphorbol-13-acetate-induced Changes in Sulfated Proteoglycan Synthesis in Cultured Chondroblasts," Cancer Res., (1980), vol. 40:7, pp. 2461-2464.

Pacifici et al., "Changes in the Sulfated Proteoglycans Synthesized by "Aging" Chondrocytes," J. Biol. Chem., (1981), vol. 256:2, pp. 1029-1037.

Perka C. et al., "Matrix-Mixed Culture: New Methodology for Chondrocyte Culture and Preparation of Cartilage Transplants," J. Biomed. Mater. Res., (2000), vol. 49, pp. 305-311.

Phinney et al., "Plastic Adherent Stromal Cells from the Bone Marrow of Commonly Used Strains of Inbred Mice: Variation in Yield, Growth, and Differentiation," J. Cell Biochem., (1999), vol. 72:4, pp. 570-585.

Remy-Martin et al., "Vascular Smooth Muscle Differentiation of Murine Stroma: A Sequential Model," Exp. Hematol., (1999), vol. 27.12, pp. 1782-1795.

Saladin et al., "Differential Regulation of Peroxisome Proliferator Activatec Receptor y1 (PPARy1) and PPARy2 Messenger RNA Expression in the Early Stages of Adipogenesis[1]," Cell Growth & Differentiation, (1999), 10, 43.

Sechriest VF. et al., "GAG-Augmented Polysaccharide Hydrogel: A Novel Biocompatible and Biodegradable Material to Support Chondrogenesis," J. Biomed. Mater. Res., (2000), vol. 49, pp. 534-541.

Solursh et al., "Stage- and Position-Related Changes in Chondrogenic Response of Chick Embryonic Wing Mesenchyme to Treatment with Dibutyryl Cyclic AMP," Development Biology, (1981), vol. 83, pp. 9-19.

Solursh, "Formation of Cartilage Tissue In Vitro," J. Cell Biochem., (1991), vol. 45, pp. 258-260.

Sommer B. et al., "Efficient Gene Transfer into Normal Human Skeletal Cells Using Recombinant Adenovirus and Conjugated Adenovirus-DNA Complexes," Calif. Tissue Int., (1999), vol. 64, pp. 45-49.

Swalla et al., "The Independence of Myogenesis and Chondrogenesis in Micromass Cultures of Chick Wing Buds," Developmental Biology, (1986), vol. 116, pp. 31-38.

Von der Mark et al., "Relationship Between Cell Shape and Type of Collagen Synthesised as Chondrocytes Lose Their Cartilage Phenotype in Culture," Nature, (1977), vol. 267: 5611, pp. 531-532.

West et al., "Fibronectin Alters the Phenotypic Properties of Cultured Chick Embryo Chondroblasts," Cell, (1979), vol. 17:3, pp. 491-501.

Yoo et al., "The Chondrogenic Potential of Human Bone-Marrow-Derived Mesenchymal Progenitor Cells," J Bone Joint Surg. Am., (1988), vol. 80:12, pp. 1745-1757.

Zuk et al., "Multilineage Cells from Human Adipose Tissue: Implications for Cell-Based Therapies," Tissue Engineering, (2001), 7, 2, 211.

- Immunodetection of collagen type II in human adipose stromal cells from monolayer cultures: Phase contrast (upper), Immunofluorescence (lower)

- Immunodetection of collagen type II in human adipose stromal cells from pellet cultures: Phase contrast (upper), Immunofluorescence (lower)

- Immunodetection of collagen type II in human adipose stromal cells from alginate cultures: Phase contrast (upper), Immunofluorescence (lower)

Collagen VI

2 Wk Alginate

Control    TGFβ

USE OF ADIPOSE TISSUE-DERIVED STROMAL CELLS FOR CHONDROCYTE DIFFERENTIATION AND CARTILAGE REPAIR

CROSS-REFERENCE TO RELATED APPLICATIONS

The present application is a divisional of U.S. application Ser. No. 10/125,106, filed Apr. 18, 2002 now U.S. Pat. No. 6,841,150, now allowed, which is a continuation of U.S. application Ser. No. 09/573,989, filed May 17, 2000, now U.S. Pat. No. 6,429,013, which claims the benefit of priority under 35 U.S.C. § 119(e) to U.S. Provisional Patent Application 60/149,850, filed Aug. 19, 1999.

FIELD OF INVENTION

The present invention relates to methods and compositions for directing adipose-derived stromal cells cultivated in vitro to differentiate into cells of the chondrocyte lineage and particularly to such directed lineage induction prior to, or at the time of, their implantation into a recipient or host for the therapeutic treatment of pathologic conditions in humans and other species.

BACKGROUND OF THE INVENTION

Mesenchymal stem cells (MSCs) are the formative pluripotent blast or embryonic-like cells found in bone marrow, blood, dermis, and periosteum that are capable of differentiating into specific types of mesenchymal or connective tissues including adipose, osseous, cartilaginous, elastic, muscular, and fibrous connective tissues. The specific differentiation pathway which these cells enter depends upon various influences from mechanical influences and/or endogenous bioactive factors, such as growth factors, cytokines, and/or local microenvironmental conditions established by host tissues.

In prenatal organisms, the differentiation of MSCs into specialized connective tissue cells is well established; for example embryonic chick, mouse or human limb bud mesenchymal cells differentiate into cartilage, bone and other connective tissues (Caplan A I (1981) In: 39th Annual Symposium of the Society for Developmental Biology, ed by S. Subtelney and U Abbott, pp 3768. New York, Alan R Liss Inc; Elmer et al. (1981) Teratology, 24:215–223; Hauschka S. D. (1974) *Developmental Biology* (1974) 37:345–368; Solursh et al. (1981) *Developmental Biology*, 83:9–19; Swalla et. al. (1986) *Developmental Biology*, 116: 31–38. In addition, a clonal rat fetus calvarial cell line has also been shown to differentiate into muscle, fat, cartilage, and bone (Goshima et al. (1991) *Clin Orthop Rel Res.* 269:274–283. The existence of MSCs in post-natal organisms has not been widely studied with the objective of showing the differentiation of post-embryonic cells into several mesodermal phenotypes. The few studies which have been done involve the formation of bone and cartilage by bone marrow cells following their encasement in diffusion chambers and in vivo transplantation (Ashton et al. (1980) *Clin Orthop Rel Res,* 151:294–307; Bruder et al. (1990) *Bone Mineral,* 11:141–151, 1990). Recently, cells from chick periosteum have been isolated, expanded in culture, and, under high density conditions in vitro, shown to differentiate into cartilage and bone (Nakahara et al. (1991) *Exp Cell Res,* 195:492–503). Rat bone marrow-derived mesenchymal cells have been shown to have the capacity to differentiate into osteoblasts and chondrocytes when implanted in vivo (Dennis et al. (1991) *Cell Transpl,* 1:2332; Goshima et al. (1991) *Clin Orthop Rel Res.* 269: 274–283). Work by Johnstone et al. U.S. Pat. No. 5,908,784 has shown the ability of mesenchymal cells derived from skin to differentiate into cells biochemically and phenotypically similar to chondrocytes.

The adult bone marrow microenvironment is a potential source for these hypothetical mesodermal stem cells. Cells isolated from adult marrow are referred to by a variety of names, including stromal cells, stromal stem cells, mesenchymal stem cells (MSCs), mesenchymal fibroblasts, reticular-endothelial cells, and Westen-Bainton cells (Gimble et al. (November 1996) *Bone* 19(5): 421–8). In vitro studies have determined that these cells can differentiate along multiple mesodermal or mesenchymal lineage pathways. These include, but are not limited to, adipocytes (Gimble, et al. (1992) *J. Cell Biochem.* 50:73–82, chondrocytes; Caplan, et al. (1998) *J Bone Joint Surg. Am.* 80(12):1745–57; hematopoietic supporting cells, Gimble, et al. (1992) *J. Cell Biochem.* 50:73–82; myocytes, Prockop, et al. (1999) *J. Cell Biochem.* 72(4):570–85; myocytes, Charbord, et al. (1999) *Exp. Hematol.* 27(12):1782–95; and osteoblasts, Beresford et al. (1993) *J. Cell Physiol.* 154:317–328). The bone marrow has been proposed as a source of stromal stem cells for the regeneration of bone, cartilage, muscle, adipose tissue, and other mesenchymal derived organs. The major limitations to the use of these cells are the difficulty and risk attendant upon bone marrow biopsy procedures and the low yield of stem cells from this source.

Adipose tissue offers a potential alternative to the bone marrow as a source of multipotential stromal stem cells. Adipose tissue is readily accessible and abundant in many individuals. Obesity is a condition of epidemic proportions in the United States, where over 50% of adults exceed the recommended BMI based on their height. Adipocytes can be harvested by liposuction on an outpatient basis. This is a relatively non-invasive procedure with cosmetic effects that are acceptable to the vast majority of patients. It is well documented that adipocytes are a replenishable cell population. Even after surgical removal by liposuction or other procedures, it is common to see a recurrence of adipocytes in an individual over time. This suggests that adipose tissue contains stromal stem cells which are capable of self-renewal.

Pathologic evidence suggests that adipose-derived stromal cells are capable of differentiation along multiple mesenchymal lineages. The most common soft tissue tumor, liposarcomas, develop from adipocyte-like cells. Soft tissue tumors of mixed origin are relatively common. These may include elements of adipose tissue, muscle (smooth or skeletal), cartilage, and/or bone. Just as bone forming cells within the bone marrow can differentiate into adipocytes or fat cells, the extramedullary adipocytes are capable of forming osteoblasts (Halvorsen WO 99/28444).

Cartilage is a hyperhydrated structure with water comprising 70% to 80% of its weight. The remaining 20% to 30% comprises type II collagen and proteoglycan. The collagen usually accounts for 70% of the dry weight of cartilage (in "Pathology" (1988) Eds. Rubin & Farber, J. B. Lippincott Company, PA. pp. 1369–1371). Proteoglycans are composed of a central protein core from which long chains of polysaccharides extend. These polysaccharides, called glycosaminoglycans, include: chondroitin-4-sulfate, chondroitin-6-sulfate, and keratan sulfate. Cartilage has a characteristic structural organization consisting of chondrogenic cells dispersed within an endogenously produced and secreted extracellular matrix. The cavities in the matrix which contain the chondrocytes are called cartilage lacunae. Unlike bone, cartilage is neither innervated nor penetrated by either the vascular or lymphatic systems (Clemente (1984) in "Gray's Anatomy, 30.sup.th Edit," Lea & Febiger).

Three types of cartilage are present in mammals and include: hyaline cartilage; fibrocartilage and elastic cartilage (Rubin and Farber, supra). Hyaline cartilage consists of a gristly mass having a firm, elastic consistency, is translucent and is pearly blue in color. Hyaline cartilage is predominantly found on the articulating surfaces of articulating joints. It is found also in epiphyseal plates, costal cartilage, tracheal cartilage, bronchial cartilage and nasal cartilage. Fibrocartilage is essentially the same as hyaline cartilage except that it contains fibrils of type I collagen that add tensile strength to the cartilage. The collagenous fibers are arranged in bundles, with the cartilage cells located between the bundles. Fibrocartilage is found commonly in the annulus fibrosis of the invertebral disc, tendinous and ligamentous insertions, menisci, the symphysis pubis, and insertions of joint capsules. Elastic cartilage also is similar to hyaline cartilage except that it contains fibers of elastin. It is more opaque than hyaline cartilage and is more flexible and pliant. These characteristics are defined in part by the elastic fibers embedded in the cartilage matrix. Typically, elastic cartilage is present in the pinna of the ears, the epiglottis, and the larynx.

The surfaces of articulating bones in mammalian joints are covered with articular cartilage. The articular cartilage prevents direct contact of the opposing bone surfaces and permits the near frictionless movement of the articulating bones relative to one another (Clemente, supra). Two types of articular cartilage defects are commonly observed in mammals and include full-thickness and partial-thickness defects. The two-types of defects differ not only in the extent of physical damage but also in the nature of repair response each type of lesion elicits.

Full-thickness articular cartilage defects include damage to the articular cartilage, the underlying subchondral bone tissue, and the calcified layer of cartilage located between the articular cartilage and the subchondral bone. Full-thickness defects typically arise during severe trauma of the joint or during the late stages of degenerative joint diseases, for example, during osteoarthritis. Since the subchondral bone tissue is both innervated and vascularized, damage to this tissue is often painful. The repair reaction induced by damage to the subchondral bone usually results in the formation of fibrocartilage at the site of the full-thickness defect. Fibrocartilage, however, lacks the biomechanical properties of articular cartilage and fails to persist in the joint on a long term basis.

Partial-thickness articular cartilage defects are restricted to the cartilage tissue itself. These defects usually include fissures or clefts in the articulating surface of the cartilage. Partial-thickness defects are caused by mechanical arrangements of the joint which in turn induce wearing of the cartilage tissue within the joint. In the absence of innervation and vasculature, partial-thickness defects do not elicit repair responses and therefore tend not to heal. Although painless, partial-thickness defects often degenerate into full-thickness defects.

In accordance with the present invention it has been observed by the inventors that when human adipose tissue-derived stromal cells are associated in a three-dimensional format they can be induced to commit and differentiate along the chondrogenic pathway when contacted in vitro with certain chondroinductive agents or factors. The three dimensional format is critical to the in vitro chondrogenesis of the invention and the cells are—preferably condensed together, for example, as a packed or pelleted cell mass or in an alginate matrix. This invention presents examples of methods and composition for the isolation, differentiation, and characterization of adult human extramedullary adipose tissue stromal cells along the chondrocyte lineage and outlines their use for the treatment of a number of human conditions and diseases. This in vitro process is believed to recapitulate that which occurs in vivo and can be used to facilitate repair of cartilage in vivo in mammals.

SUMMARY OF INVENTION

The present invention provides methods and composition for consistent and quantitative induction of stromal cells derived from subcutaneous, mammary, gonadal, or omental adipose tissues into fully functional chondrocytes. The methods comprise incubation of isolated adipose tissue-derived stromal cells, plated at densities of 500 to 20,000 cells/cm$^2$ in a chemically defined culture medium having or supplemented with (1) a chondroinductive agent that can activate any cellular transduction pathway leading to the mature chondrocyte phenotype; (2) an antibiotic; (3) a nutrient supplement such as fetal bovine serum or horse serum; (4) ascorbate or related vitamin C analogue; and (5) a glucocorticoid or another chemical agent capable of activating the cellular glucocorticoid receptor.

The present invention also provides a method for differentiating adipose tissue derived stromal cells into chondrocytice cells by pelleting stromal cells in medium such as DMEM or alpha-MEM or RPMI 1640 and supplementing the medium with (1) a chondroinductive agent that can activate any cellular transduction pathway leading to the mature chondrocyte phenotype; (2) an antibiotic; (3) a nutrient supplement such as fetal bovine serum or horse serum; (4) ascorbate or related vitamin C analogue; and (5) a glucocorticoid or another chemical agent capable of activating the cellular glucocorticoid receptor.

The present invention also provides a method for differentiating adipose tissue derived stromal cells into chondrocytic cells by suspending the cells in a calcium alginate or other biocompatible lattice or matrix capable of supporting chondrogenesis in a three dimensional configuration.

The present invention provides methods for determining the ability of these culture conditions and agents to direct the differentiation and function of the adipose tissue-derived stromal cells, for the transduction of viral vectors carrying regulatory genes into the stromal cells, for the transfection of plasmid vectors carrying regulatory genes into the stromal cells, for the tracking and detection of functional proteins encoded by these genes, and for developing biomechanical carriers for the re-introduction of these cells into a living organism.

This invention further provides methods for the introduction of these chondrocytes into cartilage defect areas for repair.

The methods and composition have use in drug discovery for compounds and proteins with relevance to the differentiated cell-related disease states and traumatic injuries including but not limited to: anterior crucia ligament tears, full-thickness articular cartilage defects, partial-thickness articular cartilage defects.

DETAILED DESCRIPTION OF INVENTION

Figure 1:
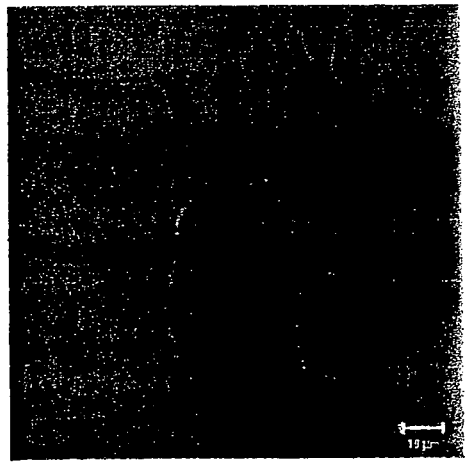
FIG. 1 shows the immunodetection of collagen type II in human adipose stromal cells from monolayer cultures. Phase contrast microscopy is used in the upper panel; Immunofluorescence is used in the lower panel.
Figure 1:
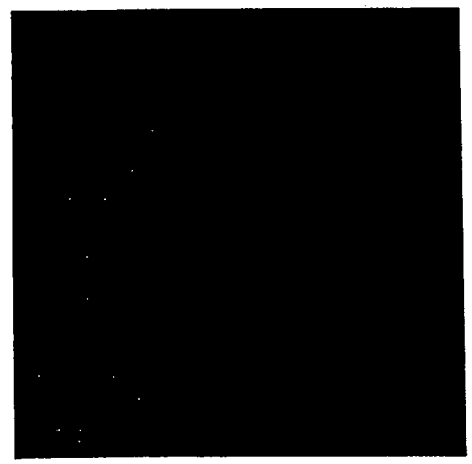

The present invention provides methods and a composition for the differentiation and culture of adipose tissue-derived stromal cells into chondrocytes. The cells produced by the methods of invention are useful in providing a source of fully differentiated and functional cells for research, transplantation, and development of tissue engineering products for the treatment of human disease and traumatic injury repair. Thus, in one aspect, the invention provides a method for differentiating adipose tissue-derived stromal cells into chondrocytes comprising culturing stromal cells in a composition which comprises a medium capable of supporting the growth and differentiation of stromal cells into functional chondrocytes. This invention further provides methods for the introduction of these chondrocytes into cartilage defect areas for repair.

"Adipose stromal cells" refers to stromal cells that originate from adipose tissue. By "adipose" is meant any fat tissue. The adipose tissue may be brown or white adipose tissue, derived from subcutaneous, omental/visceral, mammary, gonadal, or other adipose tissue site. Preferably, the adipose is subcutaneous white adipose tissue. Such cells may comprise a primary cell culture or an immortalized cell line. The adipose tissue may be from any organism having fat tissue. Preferably, the adipose tissue is mammalian, most preferably the adipose tissue is human. A convenient source of adipose tissue is from liposuction surgery, however, the source of adipose tissue or the method of isolation of adipose tissue is not critical to the invention. If stromal cells are desired for autologous transplantation into a subject, the adipose tissue will be isolated from that subject.

"Chondrocytes (cartilage cells)" refers to cells that are capable of expressing characteristic biochemical markers of chondrocytes, including but not limited to collagen type II, chondroitin sulfate, keratin sulfate and characteristic morphologic markers of smooth muscle, including but not limited to the rounded morphology observed in culture, and able to secrete collagen type II, including but not limited to the generation of tissue or matrices with hemodynamic properties of cartilage in vitro.

Any medium capable of supporting stromal cells in tissue culture may be used. Media formulations that will support the growth of fibroblasts include, but are not limited to, Dulbecco's Modified Eagle's Medium (DMEM), alpha modified Minimal Essential Medium (αMEM), and Roswell Park Memorial Institute Media 1640 (RPMI Media 1640) and the like. Typically, 0 to 20% Fetal Bovine Serum (FBS) or 1–20% horse serum will be added to the above media in order to support the growth of stromal cells and/or chondrocytes. However, a defined medium could be used if the necessary growth factors, cytokines, and hormones in FBS for stromal cells and chondrocytes are identified and provided at appropriate concentrations in the growth medium. Media useful in the methods of the invention may contain one or more compounds of interest, including, but not limited to antibiotics mitogenic or differentiative compounds for stromal cells. The cells will be grown at temperatures between 31° C. to 37° C. in a humidified incubator. The carbon dioxide content will be maintained between 2% to 10% and the oxygen content between 1% and 22%. Cells will remain in this environment for periods of up to 4 weeks.

Antibiotics which can supplemented into the medium include, but are not limited to penicillin and streptomycin. The concentration of penicillin in the chemically defined culture medium is about 10 to about 200 units per ml. The concentration of streptomycin in the chemically defined culture medium is about 10 to about 200 ug/ml.

Glucocorticoids that can be used in the invention include but are not limited to hydrocortisone and dexamethasone. The concentration of dexamethasone in the medium is about 1 to about 100 nM. The concentration of hydrocortisone in the medium is about 1 to about 100 nM.

As used herein the terms "chondroinductive agent" or "chondroinductive factor" refers to any natural or synthetic, organic or inorganic chemical or biochemical compound or combination or mixture of compounds, or any mechanical or other physical device, container, influence or force that can be applied to human adipose tissue-derived stromal cells so as to effect their in vitro chondrogenic induction or the production of chondrocytes. The chondroinductive agent is preferably selected, individually or in combination, from the group consisting of (i) a glucocorticoid such as dexamethasone; (ii) a member of the transforming growth factor-β superfamily such as a bone morphogenic protein (preferably BMP-2 or BMP-4), TGF-β1, TGF-β2, TGF-β3, insulin-like growth factor (IGF), platelet derived growth factor (PDGF), epidermal growth factor (EGF), acidic fibroblast growth factor (aFBF), basic fibroblast growth factor (bFBF), hepatocytic growth factor (HGF), keratocyte growth factor (KGF), osteogenic proteins (OP-1, OP-2, and OP-3), inhibin A or chondrogenic stimulating activity factor (CSA); (iii) a component of the collagenous extracellular matrix such as collagen I (particularly in the form of a gel); and (iv) a vitamin A analogue such as retinoic acid and; (v) ascorbate or other related vitamin C analogue.

The concentration of transforming growth factor-beta is about 1 to about 100 ng/ml. The concentration of retinoic acid is about 0.1 to about 1 ug/ml.

Examples of compounds that are stromal cell mitogens include but are not limited to transforming growth factor β; fibroblast growth factor, bone morphogenetic protein and stromal cell differentiating factors include but are not limited to dexamethasone, hydrocortisone, transforming growth factor β, fibroblast growth factor, and bone morphogenetic protein and the like.

Preferably, the adipose tissue derived stromal cells are isolated from the adipose tissue of the subject into which the final differentiated cells are to be introduced. However, the stromal cells may also be isolated from any organism of the same or different species as the subject. Any organism with adipose tissue can be a potential candidate. Preferably, the organism is mammalian, most preferably the organism is human.

The present invention also provides a method for differentiating adipose derived stromal cells into chondrocytic cells by suspending the cells in a calcium alginate or another biocompatible lattice or matrix capable of supporting chondrogenesis in a three dimensional configuration. Examples of lattice materials include (1) calcium alginate, a polysaccharide of cross linked L-glucuronic and D-mannuronic acid, at concentrations of between 1% to 4%; (2) fibrin; (3) collagen type II; or (4) agarose gel. The lattices or matrixes containing the cells are transferred to culture dishes containing: (1) a chondroinductive agent that can activate any cellular transduction pathway leading to the mature chondrocyte phenotype; (2) an antibiotic; (3) a nutrient supplement such as fetal bovine serum or horse serum; (4) ascorbate or related vitamin C analogue; and (5) a glucocorticoid or another chemical agent capable of activating the cellular glucocorticoid receptor.

The adipose tissue derived stromal cells may be stably or transiently transfected or transduced with a nucleic acid of interest using a plasmid, viral or alternative vector strategy. Nucleic acids of interest include, but are not limited to, those encoding gene products which enhance the production of extracellular matrix components found in cartilage; examples include transforming growth factor β, bone morphogentic protein, activin and insulin-like growth factor.

The transduction of viral vectors carrying regulatory genes into the stromal cells can be performed with viral vectors (adenovirus, retrovirus, adeno-associated virus, or other vector) purified by cesium chloride banding or other method at a multiplicity of infection (viral units:cell) of between 10:1 to 2000:1. Cells will be exposed to the virus in serum free or serum-containing medium in the absence or presence of a cationic detergent such as polyethyleneimine or Lipofectamine™ for a period of 1 hour to 24 hours (Byk T. et al. (1998) *Human Gene Therapy* 9:2493–2502; Sommer B et al. (1999) *Calcif. Tissue Int.* 64:45–49).

The transfection of plasmid vectors carrying regulatory genes into the stromal cells can be introduced into the cells in monolayer cultures by use of calcium phosphate DNA precipitation or cationic detergent methods (Lipofectamine™, DOTAP) or in three dimensional cultures by incorporation of the plasmid DNA vectors directly into the biocompatible polymer (Bonadio J. et al. (1999) *Nat. Med.* 5:753–759).

For the tracking and detection of functional proteins encoded by these genes, the viral or plasmid DNA vectors will contain a readily detectable marker gene, such as the green fluorescent protein or beta-galactosidase enzyme, both of which can be tracked by histochemical means.

For the development of biomechanical carriers for the re-introduction of the stromal cells into a living organism, the carriers include but are not limited to calcium alginate, agarose, types I, II, IV or other collagen isoform, fibrin, poly-lactic/poly-glycolic acid, hyaluronate derivatives or other materials (Perka C. et al. (2000) *J. Biomed. Mater. Res.* 49:305–311; Sechriest VF. et al. (2000) *J. Biomed. Mater. Res.* 49:534–541; Chu C R et al. (1995) *J. Biomed. Mater. Res.* 29:1147–1154; Hendrickson D A et al. (1994) *Orthop. Res.* 12:485–497).

Another object of the invention is to provide for the identification and study of compounds that enhance the differentiation of adipose tissue derived stromal cells into chondrocytes. Compounds which enhance differentiation may be of value in the treatment of partial or full cartilage defects, osteoarthritis, traumatized cartilage, cosmetic surgery of inborn defects including cleft palate or deviated septum. Methods include but are not limited to the development of three-dimensional in vitro cultures maintaining adipose tissue-derived stromal cells as chondrocytes that can be subsequently exposed to novel compounds of interest.

Any compound may be tested for its ability to affect the differentiation of adipose tissue derived stromal cells into chondrocytes. Appropriate vehicles compatible with the compound to be tested are known to those skilled in the art and may be found in the current edition of Remington's Pharmaceutical Sciences (1995, Mack Publishing Co., Easton, Pa.) the contents of which are incorporated herein by reference.

The features and advantages of the present invention will be more clearly understood by reference to the following examples, which are not to be construed as limiting the invention.

EXPERIMENTAL

Differentiation of Adipose Tissue-Derived Stromal Cells into Chondrocytes

EXAMPLE 1

In Vitro Chondrogenesis Using Dexamethasone

Stromal cells are isolated from human subcutaneous adipose tissue according to methods described in "*Methods and Composition of the Differentiation of Human Preadipocytes into Adipocytes*" Ser. No. 09/240,029 Filed Jan. 29, 1999. These cells are plated at a density of 500 to 20,000 cells per $cm^2$. The present invention contemplates that the creation of a precartilage condensation in vitro promotes chondrogenesis in mesenchymal progenitor cells derived from human adipose tissue. This is accomplished by methods including, but not limited to:

(1) The pellet culture system, which was developed for use with isolated growth plate cells (Kato et al. (1988) *PNAS* 85:9552–9556; Ballock & Reddi, *J. Cell Biol.* (1994) 126(5):1311–1318) and has been used to maintain expression of the cartilage phenotype of chondrocytes placed in culture (Solursh (1991) *J. Cell Biochem.* 45:258–260).

(2) The alginate suspension method, where cells are maintained in a calcium alginate suspension to prevent cell-cell contact and maintain a characteristic rounded morphology promoting the maintenance or acquisition of the chondrocyte phenotype.

Human adipose tissue-derived cells are isolated as described above. For pellet cultures, aliquots of 200,000 cells were centrifuged at 500 g for 10 minutes in sterile 15 ml conical polypropylene tubes in DMEM with 10% fetal bovine serum, 50 ng/ml ascorbate-2-phosphate, 100 nM dexamethasone (DEX) and then incubated at 37° C. in a 5% $CO_2$ incubator for up to 3 weeks. For alginate cultures, cells were suspended at a density of 1 million cells per ml in 1.2% calcium alginate and maintained in DMEM with 10% fetal bovine serum, 50 ng/ml ascorbate-2-phosphate, 100 nM dexamethasone (DEX) and then incubated at 37° C. in a 5% $CO_2$ incubator for up to 3 weeks. After 2 or 4 weeks, the cells were isolated, fixed and analyzed for chondrocyte lineage markers by immunohistochemistry with appropriate antibody reagents or by staining with toluidine blue to detect the presence of sulfated proteoglycans in the extracellular matrix.

Figure 2:
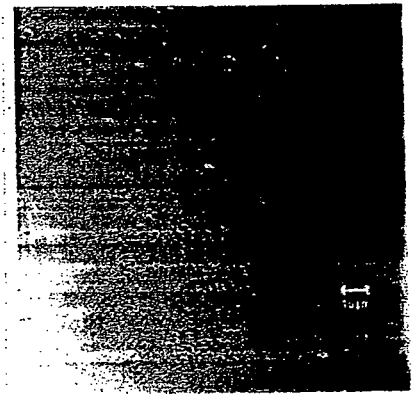
FIG. 2 shows immunodetection of collagen type II in human adipose stromal cells from pellet cultures. Phase contrast microscopy is used in the upper panel; Immunofluorescence is used in the lower panel.
Figure 2:
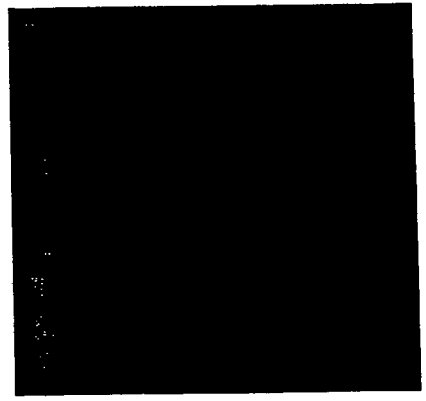
Figure 3:
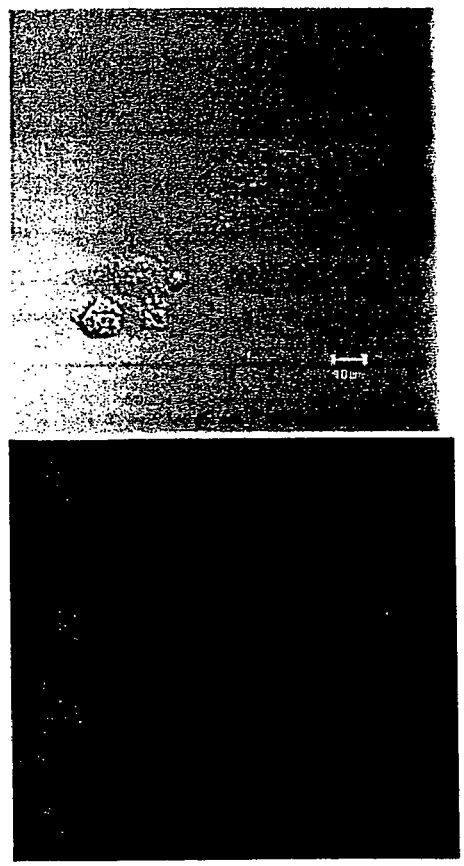
FIG. 3 shows immunodetection of collagen type II in human adipose stromal cells from alginate cultures. Phase contrast microscopy is used in the upper panel; Immunofluorescence is used in the lower panel.
Figure 4:
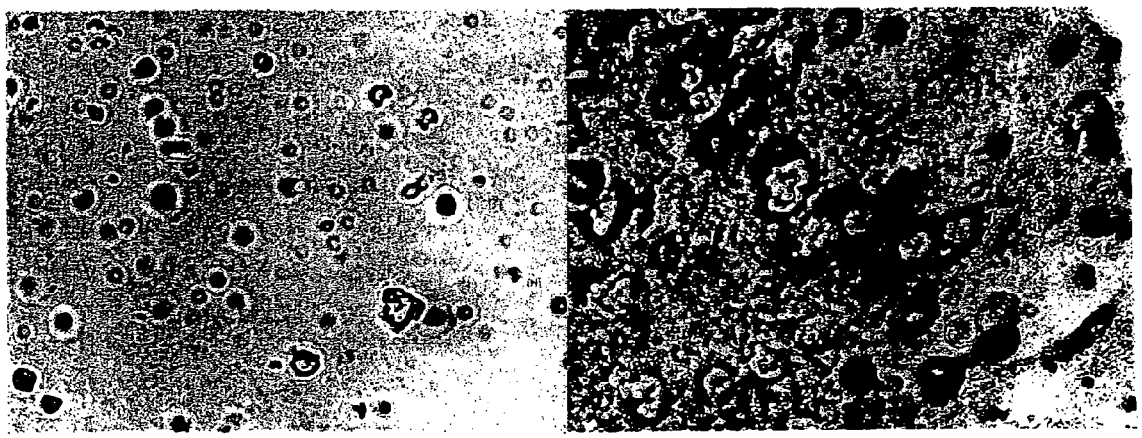
FIG. 4 shows Collagen type VI expression when cells were cultured in an alginate matrix at 2 weeks without TGF-beta (control) and with TGF-beta.

Results obtained with an antibody detecting a representative chondrocyte marker protein, collagen II, are shown in FIGS. 1–3. The cells maintained in pellet culture (FIG. 2) or calcium alginate (FIG. 3) stained positive by immunofluorescence for the intracellular presence of the collagen II protein. These results are to be contrasted with identical analysis of adipose tissue-derived cells maintained for 3 weeks in monolayer culture as shown in FIG. 1; here, no staining whatsoever is observed. Immunohistochemical results with an antibody reagent detecting the chondrocyte marker protein, collagen VI, are shown in FIG. 4. Adipose tissue-derived stromal cells were maintained in 1.2% calcium alginate and maintained in DMEM with 10% fetal bovine serum, 50 ng/ml ascorbate-2-phosphate, 100 nM dexamethasone (DEX) in the absence or presence of transforming growth factor β (10 ng/ml) and then incubated at 37° C. in a 5% $CO_2$ incubator for up to 2 weeks. Immunohistochemistry revealed a dense deposition of the collagen VI protein surrounding those cells maintained in the presence, but not the absence, of transforming growth factor β.

Figure 5:
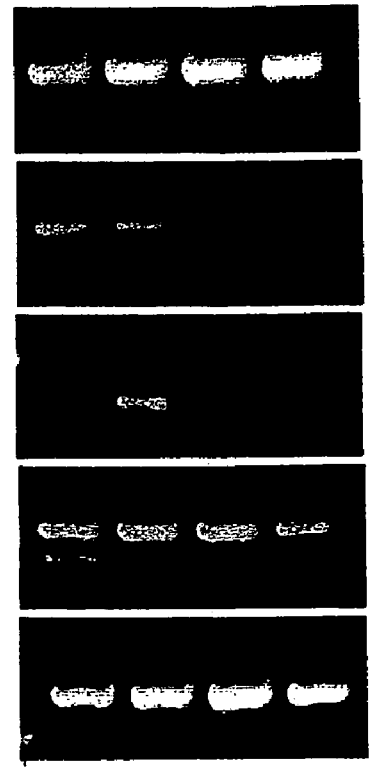
FIG. 5 shows a Western blot of results when cells were grown as monolayers or in an alginate suspension for the expression of different proteins including: collagen type VI, link, aggrecan, collagen type I, and actin.

Polymerase chain reaction results detecting representative gene markers associated with chondrogenesis are shown in FIG. 5. Adipose tissue-derived stromal cells were maintained in 1.2% calcium alginate (Alg) or in monolayer (Mono) cultures and maintained in DMEM with 10% fetal bovine serum, 50 ng/ml ascorbate-2-phosphate, 100 nM dexamethasone (DEX) in the absence (TGFβ–) or presence (TGFβ +) of transforming growth factor β (10 ng/ml) for a period of 4 weeks. Total RNA was isolated from the individual cultures and used in polymerase chain reactions with primers specific for collagens types I or VI, the proteoglycan link (Link) protein, aggrecan, or actin. The collagen markers and actin were detected under all growth conditions. However, the link mRNAs were most abundant under alginate suspension conditions and aggrecan was only present under alginate conditions in the presence of TGFβ.

These results demonstrate that, through a combination of creating an in vitro cell condensation and adding the appropriate permissive factors, we are able to produce the expression of chondrocyte markers consistent with chondrogenesis in cells from subcutaneous adipose tissue.

EXAMPLE 2

Preparation of Synthetic Cartilage Patch

Following proliferation, the chondrogenic cells still having chondrogenic potential may be cultured in an anchorage-independent manner, i.e., in a well having a cell contacting, cell adhesive surface, in order to stimulate the secretion of cartilage-specific extracellular matrix components.

Heretofore, it has been observed that chondrogenic cells proliferatively expanded in an anchorage-dependent manner usually dedifferentiate and lose their ability to secrete cartilage-specific type II collagen and sulfated proteoglycan. (Mayne et al. (1984) *Exp. Cell. Res.* 151(1): 171–82; Mayne et al. (1976) *PNAS* 73(5): 1674–8; Okayama et al. (1976) *PNAS* 73(9):3224–8; Pacifici et al. (1981) *J. Biol. Chem.* 256(2): 1029–37; Pacifici et al. (1980) *Cancer Res.* 40(7): 2461–4; Pacifici et al. (1977) *Cell* 4: 891–9; von der Mark et al. (1977) *Nature* 267(5611):531–2; West et al. (1979) *Cell* 17(3):491–501; Oegama et al. (1981) *J. Biol. Chem.* 256(2):1015–22; Benya et al. (1982) *Cell* 30(1):215–24).

It has been discovered that undifferentiated chondrogenic cells, when seeded into, and cultured in a well having a cell contacting surface that discourages adhesion of cells to the cell contacting surface, the cells redifferentiate and start to secrete cartilage-specific collagen and sulfated proteoglycans thereby to form a patch of synthetic cartilage in vitro (U.S. Pat. Nos. 5,902,741 and 5,723,331).

In addition, it has been found that culturing the cells in a pre-shaped well, enables one to manufacture synthetic cartilage patches of pre-determined thickness and volume. It is appreciated, however, that the volume of the resulting patch of cartilage is dependent not only upon the volume of the well but also upon the number of chondrogenic cells seeded into the well. Cartilage of optimal pre-determined volume may be prepared by routine experimentation by altering either, or both of the aforementioned parameters.

A. Preparation of Pre-Shaped Well.

Several approaches are available for preparing pre-shaped wells with cell contacting, cell adhesive surfaces.

The cell contacting surface of the well may be coated with a molecule that discourages adhesion of chondrogenic cells to the cell contacting surface. Preferred coating reagents include silicon based reagents i.e., dichlorodimethylsilane or polytetrafluoroethylene based reagents, i.e., Teflon.R™. Procedures for coating materials with silicon based reagents, specifically dichlorodimethylsilane, are well known in the art. See for example, Sambrook et al. (1989) "Molecular Cloning A Laboratory Manual", Cold Spring Harbor Laboratory Press, the disclosure of which is incorporated by reference herein. It is appreciated that other biocompatible reagents that prevent the attachment of cells to the surface of the well may be useful in the practice of the instant invention.

Alternatively, the well may be cast from a pliable or moldable biocompatible material that does not permit attachment of cells per se. Preferred materials that prevent such cell attachment include, but are not limited to, agarose, glass, untreated cell culture plastic and polytetrafluoroethylene, i.e., Teflon.R™. Untreated cell culture plastics, i.e., plastics that have not been treated with or made from materials that have an electrostatic charge are commercially available, and may be purchased, for example, from Falcon Labware, Becton-Dickinson, Lincoln Park, N.J. The aforementioned materials, however, are not meant to be limiting. It is appreciated that any other pliable or moldable biocompatible material that inherently discourages the attachment of chondrogenic cells may be useful in the practice of the instant invention.

The size and shape of the well may be determined by the size and shape of the articular cartilage defect to be repaired. For example, it is contemplated that the well may have a cross-sectional surface area of 25 cm.sup.2. This is the average cross-sectional surface area of an adult, human femoral chondyle. Accordingly, it is anticipated that a single piece of synthetic cartilage may be prepared in accordance with the invention in order to resurface the entire femoral chondyle. The depth of the well is preferably greater than about 0.3 cm and preferably about 0.6 cm in depth. The thickness of natural articular cartilage in an adult articulating joint is usually about 0.3 cm. Accordingly, the depth of the well should be large enough to permit a cartilage patch of about 0.3 cm to form. However, the well should also be deep enough to contain growth medium overlaying the cartilage patch.

It is contemplated also that a large piece of cartilage prepared in accordance with the invention may be "trimmed" to a pre-selected size and shape by a surgeon performing surgical repair of the damaged cartilage. Trimming may be performed with the use of a sharp cutting implement, i.e., a scalpel, a pair of scissors or an arthroscopic device fitted with a cutting edge, using procedures well known in the art.

The pre-shaped well preferably is cast in a block of agarose gel under aseptic conditions. Agarose is an economical, biocompatible, pliable and moldable material that can be used to cast pre-shaped wells, quickly and easily. As mentioned above, the dimensions of the well may dependent upon the size of the resulting cartilage plug that is desired.

A pre-shaped well may be prepared by pouring a hot solution of molten LT agarose (BioRad, Richmond, Calif.) into a tissue culture dish containing a cylinder. The cylinder having dimensions that mirror the shape of the well to be formed. The size and shape of the well may be chosen by the artisan and may be dependent upon the shape of the articular cartilage defect to be repaired. Once the agarose has cooled and solidified around the cylinder, the cylinder is carefully removed with forceps. The surface of the tissue culture dish that is exposed by the removal of the cylinder is covered with molten agarose. This seals the bottom of the well and provides a cell adhesive surface at the base of the well. When the newly added molten LT agarose cools and solidifies, the resulting pre-shaped well is suitable for culturing, and stimulating the redifferentiation of proliferated chondrogenic cells. It is appreciated, however, that alternative methods may be used to prepare a pre-shaped well useful in the practice of the invention.

B. Growth of Cartilage Patch.

Proliferated chondrogenic cells in suspension may be seeded into and cultured in the pre-shaped well. The cells may be diluted by the addition of cell culture medium to a cell density of about $1 \times 10^5$ to $1 \times 10^9$ chondrogenic cells per ml. A preferred cell culture medium comprises DMEM supplemented with 10% fetal bovine serum.

Within about four hours of seeding the chondrogenic cells into the well, the cells may coalesce to form a cohesive plug of cells. After about 4–10 days, the cells will start to secrete cartilage-specific sulfated proteoglycans and type II collagen. After prolonged periods of time in culture the collagen expressed by the chondrogenic cells in the well will be predominantly type II collagen. It is contemplated however, that the cohesive plug of cells formed within four hours may be removed from the well and surgically implanted into the cartilage defect. It is anticipated that the undifferentiated chondrogenic cells subsequently may redifferentiate in situ thereby to form synthetic cartilage within the joint.

It is contemplated that chondrocytic differentiation or stimulatory factors may be added to the chondrogenic cells in the pre-shaped well to enhance or stimulate the production of articular cartilage specific proteoglycans and/or collagen (Luyten & Reddi (1992) in "Biological Regulation of the Chondrocytes", CRC Press, Boca Raton, Ann Arbor, London, and Tokyo, p.p. 227–236). Preferred growth factors include, but are not limited to transforming growth factor-β (TGF-β), insulin-like growth factor (IGF), platelet derived growth factor (PDGF), epidermal growth factor (EGF), acidic fibroblast growth factor (aFBF), basic fibroblast growth factor (bFBF), hepatocytic growth factor, (HGF) keratinocyte growth factor (KGF), the bone morphogenic factors (BMPs) i.e., BMP-1, BMP-2, BMP-3, BMP-4, BMP-5 and BMP-6 and the osteogenic proteins (OPs), i.e. OP-1, OP-2 and OP-3. Preferred concentrations of TGF-β, IGF, PDGF, EGF, aFBF, bFBF, HGF, and KGF, range from about 1 to 100 ng/ml. Preferred concentrations of the BMP's and OP's range from about 1 to about 500 ng/ml.

However, these particular growth factors are not limiting. Any polypeptide growth factor capable of stimulating or inducing the production of cartilage specific proteoglycans and collagen may be useful in the practice of the instant invention.

In addition, it is contemplated that ascorbate may be added to the chondrogenic cells in the pre-shaped well to enhance or stimulate the production of cartilage specific proteoglycans and collagen. Preferred concentrations of ascorbate range from about 1 to about 1000 µg/ml.

EXAMPLE 3

Surgical Repair of Articular Cartilage Defect

Cartilage defects in mammals are readily identifiable visually during arthroscopic examination or during open surgery of the joint. Cartilage defects may also be identified inferentially by using computer aided tomography (CAT scanning), X-ray examination, magnetic resonance imaging (RI), analysis of synovial fluid or serum markers or by any other procedures known in the art. Treatment of the defects can be effected during an arthroscopic or open surgical procedure using the methods and compositions disclosed herein.

Accordingly, once the defect has been identified, the defect may be treated by the following steps of (1) surgically implanting at the pre-determined site, a piece of synthetic articular cartilage prepared by the methodologies described herein, and (2) permitting the synthetic articular cartilage to integrate into pre-determined site.

The synthetic cartilage patch optimally has a size and shape such that when the patch is implanted into the defect, the edges of the implanted tissue contact directly the edges of the defect. In addition, the synthetic cartilage patch may be fixed in placed during the surgical procedure. This can be effected by surgically fixing the patch into the defect with biodegradable sutures, i.e., (Ethicon, Johnson & Johnson) and/or by applying a bioadhesive to the region interfacing the patch and the defect. Preferred bioadhesives include, but are not limited to: fibrin-thrombin glues similar to those disclosed in Fr. Pat. No. 2 448 900; Fr. Pat. No. 2 448 901 and EP.S.N. 88401961.3 and synthetic bioadhesives similar to those disclosed in U.S. Pat. No. 5,197,973. It is contemplated, however, that alternative types of sutures and biocompatible glues may be useful in the practice of the invention.

In some instances, damaged articular cartilage maybe surgically excised prior the to implantation of the patch of synthetic cartilage. Additionally, the adhesion of the synthetic cartilage patch to the articular cartilage defect may be enhanced by treating the defect with transglutaminase (Ichinose et al. (1990) J. Biol. Chem. 265(3):13411–13414; Najjar et al. (1984) in "Transglutaminases", Boston, Martinuse-Nijhoff). Initially, the cartilage defect is dried, for example by using cottonoid, and filled with a solution of transglutaminase. The solution is subsequently removed, for example, by aspiration, leaving a film containing transglutaminase upon the cartilage. The synthetic cartilage patch is implanted subsequently into the defect by the methods described above.

In addition the synthetic cartilage may be useful in the repair of human articular cartilage defects. Accordingly, chondrogenic cells may be differentiated from human adipose tissue-derived stromal cells, i.e, human subcutaneous adipose tissue.

Surgical procedures for effecting the repair of articular cartilage defects are well known in the art. See for example: Luyten & Reddi (1992) in "Biological Regulation of the Chondrocytes", CRC Press, Boca Raton, Ann Arbor, London, & Tokyo, p.p. 227–236, the disclosure of which is incorporated by reference herein.

The above demonstrates a culture system in which human adipose tissue-derived stromal cells differentiate into hypertrophic chondrocytes. Since all components are defined, the system can be used for studies of the effects of growth factors etc. on the progression of chondrogenesis. In vitro systems have been used by us and others to show that these cell populations have osteogenic and adipocytic potential. We demonstrate here that this population has chondrogenic potential. This has clinical applicability for cartilage repair.

The invention also provides a process for inducing chondrogenesis in human adipose tissue-derived stromal cells by contacting such cells with a chondroinductive agent in vitro where the stromal cells are associated in a three dimensional format.

The invention also provides a process for using in vitro differentiated chondrocytes from adipose-derived stromal cells in the repair of cartilage tissue in mammals, including humans.

In the above methods, the stromal cells are preferably isolated, culture expanded human adipose tissue-derived stromal cells in a chemically defined environment and are condensed into close proximity, such as in the form of a three dimensional cell mass, e.g. packed cells or a centrifugal cell pellet. Further, the contacting preferably comprises culturing a pellet of human adipose tissue-derived stromal cells in a chemically defined medium which comprises DMEM with 10% serum, 50 ng/ml ascorbate-2-phosphate, $10^{-7}$ M dexamethasone. The differentiated cells are then introduced into the surgery site to repair cartilage. Since all components of the system are defined, the system can be used as a product for cartilage repair in mammals, including man and horses.

That which is claimed:

1. A method of producing a synthetic cartilage patch, the method comprising:
   a) culturing an adipose tissue derived stromal cell in a differentiation medium, wherein said adipose tissue derived stromal cell differentiates into a chondrocytic cell;
   b) introducing said chondrocytic cell to a pre-shaped well, wherein said pre-shaped well is a biocompatible matrix capable of supporting chondro genesis; and
   c) culturing said chondrocytic cell in said pre-shaped well, wherein said chondrocytic cell secretes a cartilage-specific extracellular matrix component to produce said synthetic cartilage patch.

2. The method of claim 1, wherein said biocompatible matrix is selected from the group consisting of calcium alginate, agarose, fibrin, and collagen.

3. The method of claim 1, wherein said cartilage-specific extracellular matrix component is cartilage-specific sulfated proteoglycans and type II collagen.

4. The method of claim 1, wherein said differentiation medium comprises (i) a chondroinductive agent capable of activating any cellular transduction pathway leading to the mature chondrocyte phenotype (ii) an antibiotic (iii) a nutrient supplement (iv) ascorbate or related vitamin C analogue and (v) a glucocorticoid or other chemical agent capable of activating the cellular glucocorticoid receptor.

5. The method of claim 4, wherein said chondroinductive agent is selected individually or in combination from the group consisting of: a glucocorticoid; a member of the transforming growth factor-beta superfamily; a collagenous extracellular matrix molecule; and a vitamin A analog.

6. The method of claim 4, wherein said antibiotic is perncillin.

7. The method of claim 4, wherein said antibiotic is streptomycin.

8. The method of claim 5, wherein said chondroinductive agent is hydrocortisone.

9. The method of claim 5, wherein said chondroinductive agent is dexamethasone.

10. The method of claim 9, wherein the concentration of dexamethasone is from about 1 to about 100 nM.

11. The method of claim 5, wherein said transforming growth factor-beta is selected from the group consisting of: bone morphogenic protein-2, bone morphogenic protein-4, TGF-$\beta$1 (transforming growth factor-beta-1), TGF-$\beta$2 (transforming growth factor-beta-2), TGF-$\beta$3 (transforming growth factor-beta-3), IGF (insulin-like growth factor), PDGF (platelet-derived growth factor), EGF (epidermal growth factor), aFBF (acidic fibroblast growth factor), bFBF (basic fibroblast growth factor), HGF (hepatocytic growth factor), KGF (keratocyte growth factor), inhibin A, and chondrogenic stimulating factor.

12. The method of claim 5, wherein said collagenous extracellular matrix molecule is collagen I.

13. The method of claim 5, wherein said vitamin A analog is retinoic acid.

14. The method of claim 6, wherein the concentration of penicillin is from about 10 to about 200 units per ml.

15. The method of claim 7, wherein the concentration of streptomycin is from about 10 to about 200 μg per ml.

16. The method of claim 8, wherein the concentration of hydrocortisone is from about 1 to about 100 nM.

17. The method of claim 11, wherein the concentration of transforming growth factor-beta is from about 1 to about 100 ng per ml.

18. The method of claim 11, wherein the concentration of TGF-$\beta$1 is from about 1 ng/ml to about 10 ng/ml.

19. The method of claim 13, wherein the concentration of retinoic acid is about 0.1 ng per ml to about 1 μg per ml.

* * * * *